(12) United States Patent
Osawa et al.

(10) Patent No.: US 11,344,204 B2
(45) Date of Patent: May 31, 2022

(54) PHOTOACOUSTIC MEASUREMENT PROBE AND PROBE UNIT AND PHOTOACOUSTIC MEASUREMENT APPARATUS INCLUDING THE SAME

(71) Applicant: FUJIFILM Corporation, Tokyo (JP)

(72) Inventors: Atsushi Osawa, Ashigarakami-gun (JP); Atsushi Hashimoto, Ashigarakami-gun (JP); Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1197 days.

(21) Appl. No.: 15/642,907

(22) Filed: Jul. 6, 2017

(65) Prior Publication Data

US 2017/0296063 A1  Oct. 19, 2017

Related U.S. Application Data

(63) Continuation of application No. PCT/JP2015/084107, filed on Dec. 4, 2015.

(30) Foreign Application Priority Data

Jan. 8, 2015  (JP) .............................. JP2015-002676
Sep. 18, 2015  (JP) .............................. JP2015-184763

(51) Int. Cl.
*A61B 5/00* (2006.01)
*A61B 8/13* (2006.01)
*A61B 5/02* (2006.01)

(52) U.S. Cl.
CPC .......... *A61B 5/0095* (2013.01); *A61B 5/7203* (2013.01); *A61B 8/13* (2013.01);
(Continued)

(58) Field of Classification Search
None
See application file for complete search history.

(56) References Cited

U.S. PATENT DOCUMENTS 5,433,207 A * 7/1995 Pretlow, III ......... G01N 29/032
600/458
9,702,854 B2 * 7/2017 Kim .................... G01N 29/2418
(Continued)

FOREIGN PATENT DOCUMENTS

EP        2805672 A2   11/2014
JP     2012-166009 A    9/2012
(Continued)

OTHER PUBLICATIONS

Machine translation of JP 2013-255707 (Year: 2020).*
(Continued)

*Primary Examiner* — Luther Behringer
(74) *Attorney, Agent, or Firm* — Birch, Stewart, Kolasch & Birch, LLP

(57) ABSTRACT

A photoacoustic measurement probe and a probe unit capable of preventing generation of artifacts in a photoacoustic measurement apparatus are obtained. In a photoacoustic measurement probe having a light emitting unit that emits measurement light toward a subject, an acoustic wave detection element that detects an acoustic wave emitted from a portion of the subject that has received the measurement light, and a housing which has a surface facing the subject at the time of use and in which the light emitting unit and the acoustic wave detection element are housed, at least one slit that is opened to the housing surface and that extends from the housing surface toward the inside of the housing is provided between the light emitting unit and the acoustic wave detection element.

19 Claims, 9 Drawing Sheets

(52) U.S. Cl.
CPC ... *A61B 5/02007* (2013.01); *A61B 2562/0204* (2013.01); *A61B 2576/00* (2013.01)

(56) References Cited

U.S. PATENT DOCUMENTS

| | | | |
|---|---|---|---|
| 2013/0310694 | A1 | 11/2013 | Tsujita et al. |
| 2014/0340685 | A1* | 11/2014 | Kim ..................... A61B 5/0095 356/432 |
| 2014/0343394 | A1 | 11/2014 | Irisawa et al. |

FOREIGN PATENT DOCUMENTS

| | | |
|---|---|---|
| JP | 2012-179350 A | 9/2012 |
| JP | 2013-176542 A | 9/2013 |
| JP | 2013-255707 A | 12/2013 |

OTHER PUBLICATIONS

Extended European Search Report, dated Jul. 16, 2018, for European Application No. 15876976.0.

International Preliminary Report on Patentability and English Translation of the Written Opinion of the International Searching Authority (Forms PCT/IB/326, PCT/IB/373 and PCT/ISA/237) for International Application No. PCT/JP2015/084107, dated Jul. 20, 2017.
European Office Action for corresponding European Application No. 15876976.0, dated Mar. 31, 2020.
International Search Report, issued in PCT/JP2015/084107, PCT/ISA/210, dated Feb. 16, 2016.
Written Opinion of the International Searching Authority, issued in PCT/JP2015/084107, PCT/ISA/237, dated Feb. 16, 2016.
European Office Action, dated Sep. 17, 2020 for European Application No. 15876976.0.
Japanese Notification of Reasons for Refusal, dated Jan. 9, 2018, for corresponding Japanese Application No. 2015-184763, with an English machine translation.
European Summons to Attend Oral Proceedings Pursuant to Rule 115(1) EPC for corresponding European Application No. 15876976.0, dated Feb. 3, 2022.

* cited by examiner

PRIOR ART

PHOTOACOUSTIC MEASUREMENT PROBE AND PROBE UNIT AND PHOTOACOUSTIC MEASUREMENT APPARATUS INCLUDING THE SAME

CROSS-REFERENCE TO RELATED APPLICATIONS

This application is a Continuation of PCT International Application No. PCT/JP2015/084107 filed on Dec. 4, 2015, which claims priority under 35 U.S.C § 119(a) to Japanese Patent Application No. 2015-002676 filed on Jan. 8, 2015 and Japanese Patent Application No. 2015-184763 filed on Sep. 18, 2015. Each of the above application(s) is hereby expressly incorporated by reference, in its entirety, into the present application.

BACKGROUND OF THE INVENTION

1. Field of the Invention

The present invention relates to a photoacoustic measurement probe that emits light toward a subject and receives the light to detect photoacoustic waves generated within the subject.

In addition, the present invention relates to a probe unit and a photoacoustic measurement apparatus including such a probe.

2. Description of the Related Art

In recent years, a non-invasive measurement method using a photoacoustic effect has been drawing attention. In the measurement method, a photoacoustic wave, which is an elastic wave generated as a result of emission of pulsed light having an appropriate wavelength (for example, a wavelength band of visible light, near-infrared light, or intermediate infrared light) to a subject and absorption of the energy of the pulsed light by an absorbing substance in the subject, is detected to quantitatively measure the concentration of the absorbing substance. The absorbing substance in the subject is, for example, glucose or hemoglobin contained in blood. In addition, the technique of detecting such a photoacoustic wave and generating a photoacoustic image based on the detection signal is called photoacoustic imaging (PAI) or photo acoustic tomography (PAT).

In photoacoustic imaging, for example, as disclosed in JP2012-166009A and JP2012-179350A, a probe configured to include a light emitting unit for emitting measurement light, such as pulsed light, toward a subject, an acoustic wave detection element for detecting an acoustic wave emitted from a part of the subject irradiated with the measurement light, and a housing in which the light emitting unit and the acoustic wave detection element are housed is often used.

SUMMARY OF THE INVENTION

Conventionally, in the case of generating a photoacoustic image using the probe configured to include the light emitting unit, the acoustic wave detection element, and the housing, it has been recognized that artifacts (fake image) are likely to be generated in the photoacoustic image.

The present invention has been made in view of the above circumstances, and it is an object of the present invention to provide a photoacoustic measurement probe capable of preventing the generation of artifacts.

In addition, it is an object of the present invention to provide a probe unit and a photoacoustic measurement apparatus capable of preventing the generation of artifacts.

One photoacoustic measurement probe according to the present invention is a photoacoustic measurement probe comprising: a light emitting unit that emits measurement light toward a subject; an acoustic wave detection element that detects an acoustic wave emitted from a portion of the subject that has received the measurement light; and a housing which has a surface facing the subject at the time of use and in which the light emitting unit and the acoustic wave detection element are housed. At least one slit that is opened to the housing surface and that extends from the surface of the housing toward an inside of the housing is provided between the light emitting unit and the acoustic wave detection element, and in a plan view of the photoacoustic measurement probe from the surface side, the light emitting unit, the housing, the slit, the housing and the acoustic wave detection element are arranged in this order in an arrangement direction of the light emitting unit and the acoustic wave detection element.

In the photoacoustic measurement probe of the present invention having the configuration described above, it is preferable that, in the plan view of the photoacoustic measurement probe from the surface side, both end portions of the slit are located outside both end portions of the acoustic wave detection element in a direction perpendicular to the arrangement direction of the light emitting unit and the acoustic wave detection element.

In the photoacoustic measurement probe of the present invention having the configuration described above, it is preferable that at least one light emitting unit is disposed on each of both sides of the acoustic wave detection element with the acoustic wave detection element interposed therebetween.

As described above, in a case where at least one light emitting unit is disposed on each of both sides of the acoustic wave detection element, it is preferable that, in the slit provided between one of the light emitting units disposed on both sides of the acoustic wave detection element and the acoustic wave detection element, and in the slit provided between the other one of the light emitting units disposed on both sides of the acoustic wave detection element and the acoustic wave detection element, one ends of the slits are connected to each other and the other ends of the slits are connected to each other by another slit, such that the acoustic wave detection element is surrounded by the slits. It is preferable that another slit is not discontinuous in the middle so that the acoustic wave detection element is surrounded by the slits over the entire circumference. However, without being limited thereto, another slit described above may be discontinuous in the middle.

Another photoacoustic measurement probe according to the present invention is a photoacoustic measurement probe comprising: a light emitting unit that emits measurement light toward a subject; an acoustic wave detection element that detects an acoustic wave emitted from a portion of the subject that has received the measurement light; and a housing which has a surface facing the subject at the time of use and in which the light emitting unit and the acoustic wave detection element are housed. At least one set of materials forming an interface extending from the surface of the housing toward an inside of the housing are provided between the light emitting unit and the acoustic wave detection element, the set being obtained by bringing two materials having different acoustic impedances into close contact with each other.

In another photoacoustic measurement probe according to the present invention, it is preferable that, in a plan view of the photoacoustic measurement probe from the surface side, both end portions of the interface are located outside both end portions of the acoustic wave detection element in a direction perpendicular to an arrangement direction of the light emitting unit and the acoustic wave detection element.

In another photoacoustic measurement probe according to the present invention described above, it is preferable that at least one light emitting unit is disposed on each of both sides of the acoustic wave detection element with the acoustic wave detection element interposed therebetween.

As described above, in a case where at least one light emitting unit is disposed on each of both sides of the acoustic wave detection element, it is preferable that, in the interface present between one of the light emitting units disposed on both sides of the acoustic wave detection element and the acoustic wave detection element and the interface present between the other one of the light emitting units disposed on both sides of the acoustic wave detection element and the acoustic wave detection element, one ends are connected to each other and the other ends are connected to each other by another interface obtained by bringing materials having different acoustic impedances into close contact with each other, such that the acoustic wave detection element is surrounded by the interfaces. It is preferable that another interface described above is not discontinuous in the middle and the acoustic wave detection element is surrounded by the interfaces over the entire circumference. However, without being limited thereto, another interface described above may be discontinuous in the middle.

In another photoacoustic measurement probe according to the present invention described above, it is preferable that a slit extending from the surface of the housing toward the inside of the housing is provided between the light emitting unit and the acoustic wave detection element and a material having an acoustic impedance different from that of a material forming the housing is filled in the slit.

As described above, in a case where a material having an acoustic impedance different from that of a material forming the housing is filled in the slit, it is preferable that the material having an acoustic impedance different from that of a material forming the housing is filled over an entire depth of the slit.

Alternatively, in a case where a material having an acoustic impedance different from that of a material forming the housing is filled in the slit, it is preferable that the material having an acoustic impedance different from that of a material forming the housing is filled between a position aligned with the surface of the housing and a position shallower than the depth of the slit.

As the material having an acoustic impedance different from that of a material forming the housing, for example, a fluorinated liquid is appropriately used. The "fluorinated liquid" refers to a liquid formed of a mixture of one or more of perfluoropolyethers, perfluorocarbons, hydrofluoropolyethers, hydrofluoroethers.

In the housing, a portion surrounding the light emitting unit and a portion surrounding the acoustic wave detection element can be formed of housing materials having different acoustic impedances, and the interface can be formed by the two housing materials.

On the other hand, a probe unit according to the present invention comprises: the photoacoustic measurement probe according to the present invention described above; a light source that outputs measurement light; and a connection unit that optically connects the measurement light to the light emitting unit of the photoacoustic measurement probe.

A photoacoustic measurement apparatus according to the present invention comprises: the photoacoustic measurement probe according to the present invention described above; and a signal processing unit that generates a photoacoustic image based on a photoacoustic wave detection signal output from the photoacoustic measurement probe.

According to the research by the inventors of the present invention, it was found that artifacts could be generated by the following reasons in a photoacoustic measurement apparatus using a conventional probe. That is, when measurement light is emitted from the light emitting unit in the housing of the probe, the measurement light may be emitted to the vicinity of the surface of the housing. Then, a photoacoustic wave may be generated from a portion of the housing that has absorbed the measurement light, and the photoacoustic wave may be detected by the acoustic wave detection element to cause artifacts.

In one photoacoustic measurement probe according to the present invention, since at least one slit that is opened to the housing surface and that extends from the surface of the housing toward the inside of the housing is provided between the light emitting unit and the acoustic wave detection element, photoacoustic waves that are generated as described above to travel toward the acoustic wave detection element are reflected and attenuated on the interface between the air in the slit and the housing material. Therefore, since high-intensity photoacoustic waves are not incident on the acoustic wave detection element, the generation of artifacts is prevented.

In another photoacoustic measurement probe according to the present invention, since at least one set of materials forming an interface extending from the surface of the housing toward the inside of the housing are provided between the light emitting unit and the acoustic wave detection element and the set is obtained by bringing two materials having different acoustic impedances into close contact with each other, photoacoustic waves that are generated as described above to travel toward the acoustic wave detection element are reflected and attenuated on the interface. Therefore, since high-intensity photoacoustic waves are not incident on the acoustic wave detection element, the generation of artifacts is prevented.

DESCRIPTION OF THE PREFERRED EMBODIMENTS

Hereinafter, embodiments of the present invention will be described in detail with reference to the diagrams.

First Embodiment

Figure 1:
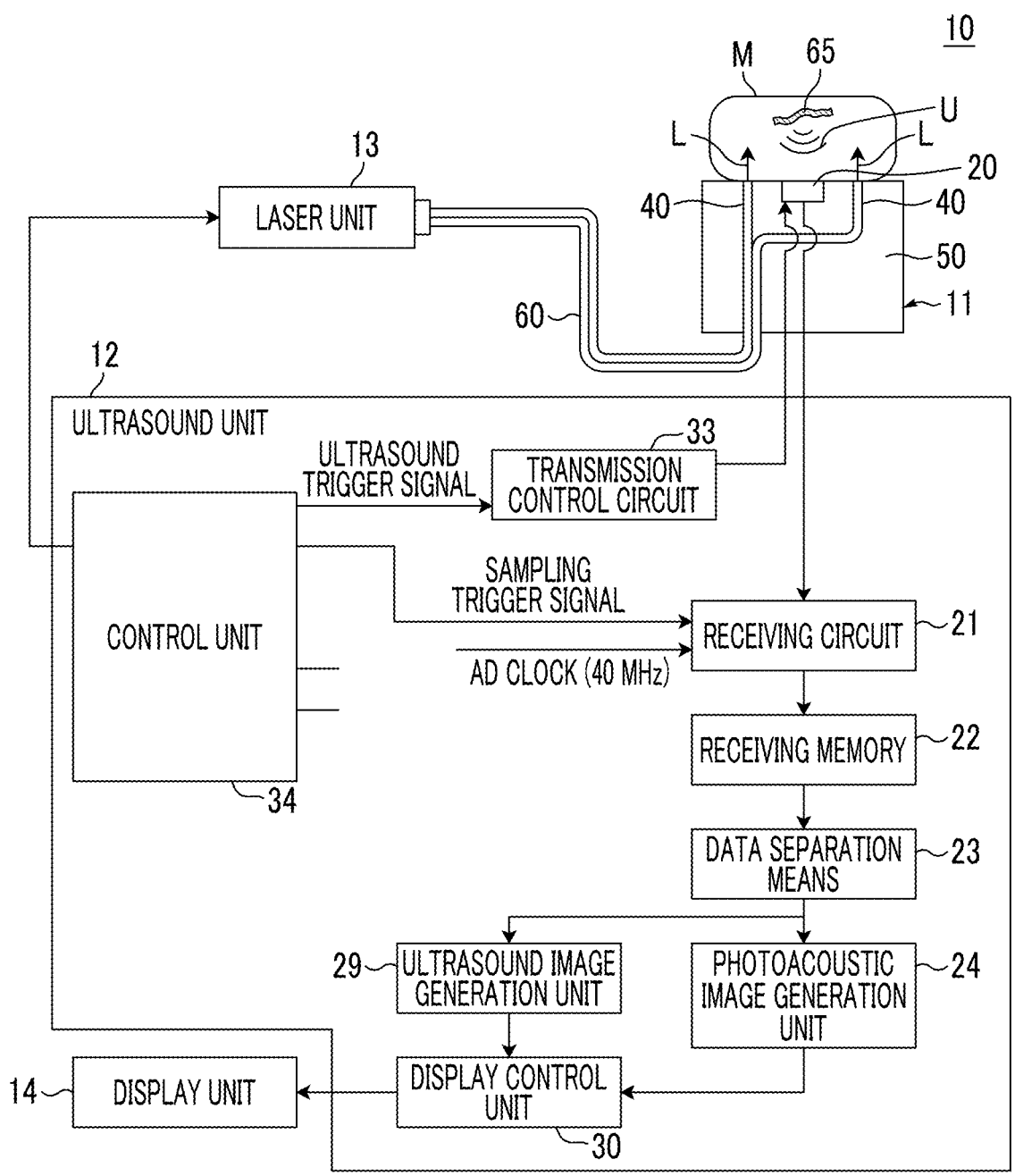
FIG. 1 is a schematic diagram showing the overall configuration of a photoacoustic measurement apparatus according to an embodiment of the present invention.
Figure 2:
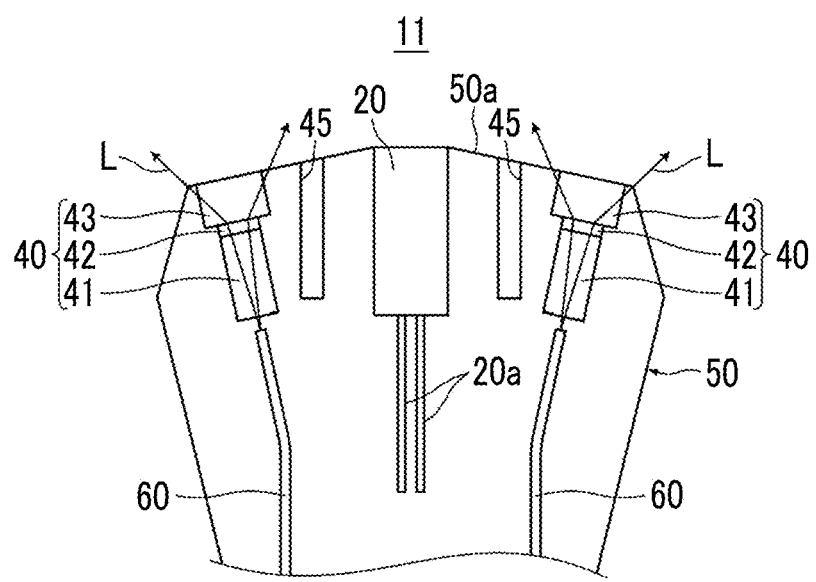
FIG. 2 is a side sectional view showing a probe according to a first embodiment of the present invention.
Figure 3:
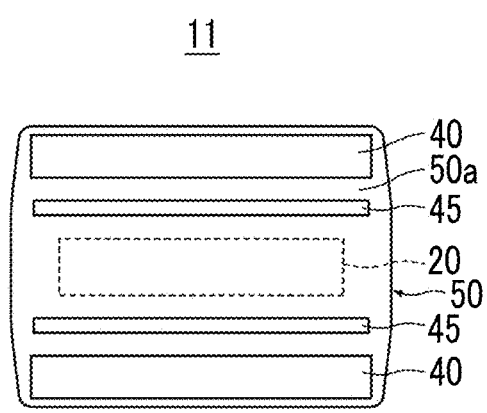
FIG. 3 is a front view of the probe shown in FIG. 2.

First, a photoacoustic measurement probe, a probe unit, and a photoacoustic measurement apparatus according to a first embodiment of the present invention will be described. FIG. 1 is a schematic diagram showing the overall configuration of a photoacoustic measurement apparatus 10 of the present embodiment, and FIGS. 2 and 3 are a side sectional view and a front view showing a photoacoustic measurement probe (hereinafter, simply referred to as a probe) 11 used in the photoacoustic measurement apparatus 10, respectively. In FIG. 1, the shape of the probe 11 is schematically shown.

As an example, the photoacoustic measurement apparatus 10 of the present embodiment has a function of generating a photoacoustic image based on a photoacoustic signal, and includes the probe (ultrasound probe) 11, an ultrasound unit 12, a laser unit 13, a display unit 14, and the like as schematically shown in FIG. 1. Hereinafter, these components will be sequentially described.

The probe 11 has, for example, a function of emitting measurement light and an ultrasound wave toward a subject M, which is a living body, and a function of detecting an acoustic wave U propagating through the subject M. That is, the probe 11 can emit (transmit) ultrasound waves to the subject M and detect (receive) reflected ultrasound waves (reflected acoustic waves) that return due to reflection from the subject M. The probe 11 can also detect photoacoustic waves generated in the subject M. In this specification, the term "acoustic wave" is a term including ultrasound waves and photoacoustic waves. Here, the "ultrasound wave" means an elastic wave transmitted by a probe and its reflected wave, and the "photoacoustic wave" means an elastic wave emitted by absorbing measurement light by the absorber 65. As the absorber 65 in the subject M, for example, blood vessels, a metal member, and the like can be mentioned.

As shown in detail in FIG. 2, the probe 11 includes a transducer array 20 that is an acoustic wave detection element, a total of two light emitting units 40 disposed on both sides of the transducer array 20 with the transducer array 20 interposed therebetween, and a housing 50 in which the transducer array 20 and the two light emitting units 40 are housed. The transducer array 20 is located, for example, at a position of about 1 mm or less from the upper end surface in FIG. 2.

In the present embodiment, the transducer array 20 also functions as an ultrasound wave transmission element. The transducer array 20 is connected to an ultrasound wave transmitting circuit and an acoustic wave receiving circuit through a wiring line 20a. An optical fiber 60 as a connection unit for guiding laser light L, which is measurement light emitted from the laser unit 13 to be described later, to the light emitting unit 40 is connected to the probe 11.

The transducer array 20 is configured to include a plurality of ultrasound transducers arranged in a one-dimensional or two-dimensional manner, for example. The ultrasound transducer is, for example, a piezoelectric element formed of a polymer film, such as piezoelectric ceramics or polyvinylidene fluoride (PVDF). The ultrasound transducer has a function of converting the received acoustic wave U into an electrical signal. The electrical signal output from the transducer array 20 is input to a receiving circuit 21 to be described later. Generally, the probe 11 corresponding to sector scanning, the probe 11 corresponding to linear scanning, the probe 11 corresponding to convex scanning, and the like are prepared. Among these, an appropriate one selected according to an imaging part is used. The transducer array 20 may include an acoustic lens.

The ultrasound transducer also has a function of transmitting ultrasound waves. That is, when an alternating voltage is applied to the ultrasound transducer, the ultrasound transducer generates ultrasound waves having a frequency corresponding to the frequency of the alternating voltage. Transmission and reception of ultrasound waves may be separated from each other. That is, for example, ultrasound waves may be transmitted from a position different from the probe 11, and reflected ultrasound waves of the transmitted ultrasound waves may be received by the probe 11.

The light emitting unit 40 is a unit that emits the laser light L guided by the optical fiber 60 to the subject M. As shown in FIGS. 2 and 3, in the present embodiment, the two light emitting units 40 are disposed on both sides of the transducer array 20, for example, in the elevation direction (in a case where a plurality of ultrasound transducers are arranged in a one-dimensional manner, a direction that is perpendicular to the arrangement direction and is parallel to the detection surface) with the transducer array 20 interposed therebetween.

The light emitting unit 40 is configured to include a first light guide member 41, a diffusion portion 42, and a second light guide member 43, as an example. The first light guide member 41, the diffusion portion 42, and the second light guide member 43 are arranged in series in the traveling direction of measurement light, and these are fixed by a fixing frame body (not shown). The first light guide member 41 may be air.

The light emitting end surface of the optical fiber 60 is optically coupled to the light incidence end surface of the first light guide member 41. As the first light guide member 41, for example, a light guide plate can be used. The light guide plate is formed by performing special processing on the surface of, for example, an acrylic plate or a quartz plate, and light incident from one end surface is emitted from the other end surface with a uniform in-plane intensity. The first light guide member 41 guides the laser light L guided by the optical fiber 60 to the diffusion portion 42.

The diffusion portion 42 diffuses the laser light L emitted from the first light guide member 41. As a result, the emission range of the laser light L is further enlarged. As the diffusion portion 42, for example, a diffusion plate can be used. As the diffusion plate, it is possible to use a lens diffusion plate in which microlenses are randomly arranged on a substrate, a quartz plate in which, for example, diffusing fine particles are dispersed, or the like. As the lens diffusion plate, a holographic diffusion plate or an engineering diffusion plate may be used. The diffusion portion 42 does not need to be a member independent from the first light guide member 41. For example, a diffusion layer may be provided in a light emitting end portion of the first light guide member 41 to form the diffusion portion 42, or a diffusion surface may be provided on the light emitting end surface to form the diffusion portion 42.

The diffusion portion 42 is fixed to a fixing member (not shown) by, for example, an adhesive, but it is preferable to use an adhesive having strong light diffusibility when attaching the lens diffusion plate. This is because, when the adhesive adheres to the lens diffusion surface, the light diffusibility of the portion is lost and there is a possibility that strong light will be emitted locally. In the case of using an adhesive having light diffusibility, light can be diffused by the light diffusibility of the adhesive even in a case where the adhesive adheres to the lens diffusion surface. As the adhesive, for example, an adhesive such as a silicone rubber containing a white pigment can be used. As the white pigment, for example, $TiO_2$ can be mentioned. The content of $TiO_2$ is preferably 1% by weight to 20% by weight. As silicone rubber, for example, liquid rubber KE-45-W manufactured by Shin-Etsu Chemical Co., Ltd. can be used.

The second light guide member 43 allows the laser light L diffused by the diffusion portion 42 to be emitted toward the subject M. The light emitting end portion of the second light guide member 43 is fitted into the optical window portion (opening portion) of the housing 50, and has a function of filling the gap of the optical window portion. Instead of providing the diffusion layer or the diffusion surface described above in the first light guide member 41, the diffusion layer or the diffusion surface may also be provided in the light incidence end portion or the light incidence end surface of the second light guide member 43.

The laser unit 13 shown in FIG. 1 has, for example, a flash lamp excitation Q-switch solid state laser, such as a Q-switch alexandrite laser, and emits the laser light L as measurement light that is emitted to the subject M. The laser unit 13 is configured to receive a trigger signal from a control unit 34 of the ultrasound unit 12 and output the laser light L, for example. It is preferable that the laser unit 13 outputs the pulsed laser light L having a pulse width of 1 to 100 nsec (nanoseconds).

The wavelength of the laser light L is appropriately selected according to the light absorption characteristics of the absorber 65 in the subject M that is a measurement target. For example, in a case where the measurement target is hemoglobin in the living body, that is, in the case of imaging blood vessels, it is generally preferable that the wavelength is a wavelength belonging to the near-infrared wavelength range. The near-infrared wavelength range means a wavelength range of approximately 700 nm to 850 nm. However, it is natural that the wavelength of the laser light L is not limited thereto. In addition, the laser light L may have a single wavelength, or may include a plurality of wavelengths of, for example, 750 nm and 800 nm. In a case where the laser light L includes a plurality of wavelengths, light beams having these wavelengths may be simultaneously emitted to the subject M, or may be emitted while being switched alternately.

In addition to the alexandrite laser described above, the laser unit 13 can be formed by using a YAG-second harmonic generation (SHG)-optical parametric oscillation (OPO) laser, a Ti-Sapphire (titanium sapphire) laser, or the like capable of outputting laser light in the near-infrared wavelength range similarly.

The laser unit 13 as a light source forms a probe unit together with the probe 11 and the optical fiber 60.

The optical fiber 60 guides the laser light L emitted from the laser unit 13 to the two light emitting units 40. The optical fiber 60 is not particularly limited, and known fibers, such as a quartz fiber, can be used. For example, one thick optical fiber may be used, or a bundle fiber in which a plurality of optical fibers are bundled may be used. As an example, in a case where a bundle fiber is used, the bundle fiber is arranged so that the laser light L is incident from the light incidence end surface of a group of fiber portions, and the light emitting units 40 are coupled to the light emitting end surfaces of the two branched fiber portions of the bundle fiber.

The ultrasound unit 12 has the receiving circuit 21, a receiving memory 22, data separation means 23, a photoacoustic image generation unit 24, an ultrasound image generation unit 29, a display control unit 30, a transmission control circuit 33, and the control unit 34.

The control unit 34 controls each unit of the photoacoustic measurement apparatus 10, and includes a trigger control circuit (not shown) in the present embodiment. The trigger control circuit transmits an optical trigger signal to the laser unit 13, for example, in the case of acquiring a photoacoustic image. As a result, the flash lamp of the excitation source is turned on in the Q-switch solid state laser of the laser unit 13, and excitation of the laser rod is started. While the excitation state of the laser rod is maintained, the laser unit 13 is ready to output the laser light L.

Thereafter, the control unit 34 transmits a Q-switch trigger signal to the laser unit 13 from the trigger control circuit. That is, the control unit 34 controls the output timing of the laser light L from the laser unit 13 using the Q-switch trigger signal. The control unit 34 transmits a sampling trigger signal to the receiving circuit 21 simultaneously with the transmission of the Q-switch trigger signal. This sampling trigger signal specifies the sampling start timing of the photoacoustic signal in an analog to digital convertor (AD converter) of the receiving circuit 21. Thus, it is possible to sample a photoacoustic signal in synchronization with the output of the laser light L by using the sampling trigger signal.

In the case of acquiring an ultrasound image, the control unit 34 transmits an ultrasound wave transmission trigger signal for giving an instruction to transmit ultrasound waves to the transmission control circuit 33. When the ultrasound wave transmission trigger signal is received, the transmission control circuit 33 makes the probe 11 transmit ultrasound waves. The control unit 34 transmits a sampling trigger signal to the receiving circuit 21 according to the timing of ultrasound wave transmission, thereby starting the sampling of a reflected ultrasound signal.

When acquiring the photoacoustic image or the ultrasound image described above, the position of the probe 11 is gradually changed in the above-described elevation direction with respect to the subject M, and the subject M is scanned with the laser light L or ultrasound waves. Therefore, sampling of the photoacoustic signal or the reflected ultrasound signal is performed while shifting the acoustic wave detection line line by line in synchronization with the scanning. The scanning may be performed by manually moving the probe 11 by the operator or may be performed using an automatic scanning mechanism.

The receiving circuit 21 receives a detection signal output from the probe 11, and stores the received detection signal in the receiving memory 22. Typically, the receiving circuit 21 is configured to include a low noise amplifier, a variable gain amplifier, a low pass filter, and an AD converter. The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 22. The receiving circuit 21 is formed by one integrated circuit (IC), for example.

In the present embodiment, the probe 11 outputs a detection signal of photoacoustic waves and a detection signal of reflected ultrasound waves. Therefore, digitized detection signals (sampling data) of photoacoustic waves and reflected ultrasound waves are stored in the receiving memory 22. The data separation means 23 reads the sampling data (photoacoustic data) of the photoacoustic wave detection signal from the receiving memory 22, and transmits the sampling data to the photoacoustic image generation unit 24. The data separation means 23 reads the sampling data (reflected ultrasound data) of the reflected ultrasound detection signal from the receiving memory 22, and transmits the sampling data to the ultrasound image generation unit 29.

The photoacoustic image generation unit 24 reconstructs data of one line by adding the pieces of photoacoustic data stored in the receiving memory 22 to each other with a delay time corresponding to the position of the transducer array 20 of the probe 11, and generates data of a tomographic image (photoacoustic image) based on the photoacoustic data of each line. The photoacoustic image generation unit 24 may perform reconstruction using a circular back projection (CBP) instead of the delay addition method. Alternatively, the photoacoustic image generation unit 24 may perform reconstruction using a Hough transform method or a Fourier transform method. The photoacoustic image generation unit 24 outputs the data of the photoacoustic image generated as described above to the display control unit 30.

As is apparent from the above description, the photoacoustic image generation unit 24 forms a signal processing unit in the photoacoustic measurement apparatus of the present invention.

The ultrasound image generation unit 29 generates data of a tomographic image (ultrasound image) by performing basically the same processing as for the photoacoustic data on the reflected ultrasound data stored in the receiving memory 22. The ultrasound image generation unit 29 outputs the data of the ultrasound image generated as described above to the display control unit 30.

The display control unit 30 displays a photoacoustic image on the display unit 14 based on the data of the photoacoustic image and displays an ultrasound image on the display unit 14 based on the data of the ultrasound image. These two images are separately displayed on the display unit 14, or are combined to be displayed on the display unit 14 as a composite image. In the latter case, the display control unit 30 performs image combination by superimposing the photoacoustic image and the ultrasound image, for example. In this manner, if the ultrasound image is generated and displayed in addition to the photoacoustic image, a portion that can not be imaged in the photoacoustic image can be observed in the ultrasound image.

Next, in the photoacoustic measurement apparatus 10 having the basic constitution as described above, the configuration of the probe 11 for preventing the generation of artifacts will be described. As shown in FIGS. 2 and 3, in the probe 11, a slit 45 is provided between the transducer array 20 and one light emitting unit 40 and between the transducer array 20 and the other light emitting unit 40. Each slit 45 is formed so as to extend from a surface 50a of the housing 50 toward the inside of the housing and be opened to the housing surface 50a.

Figure 12:
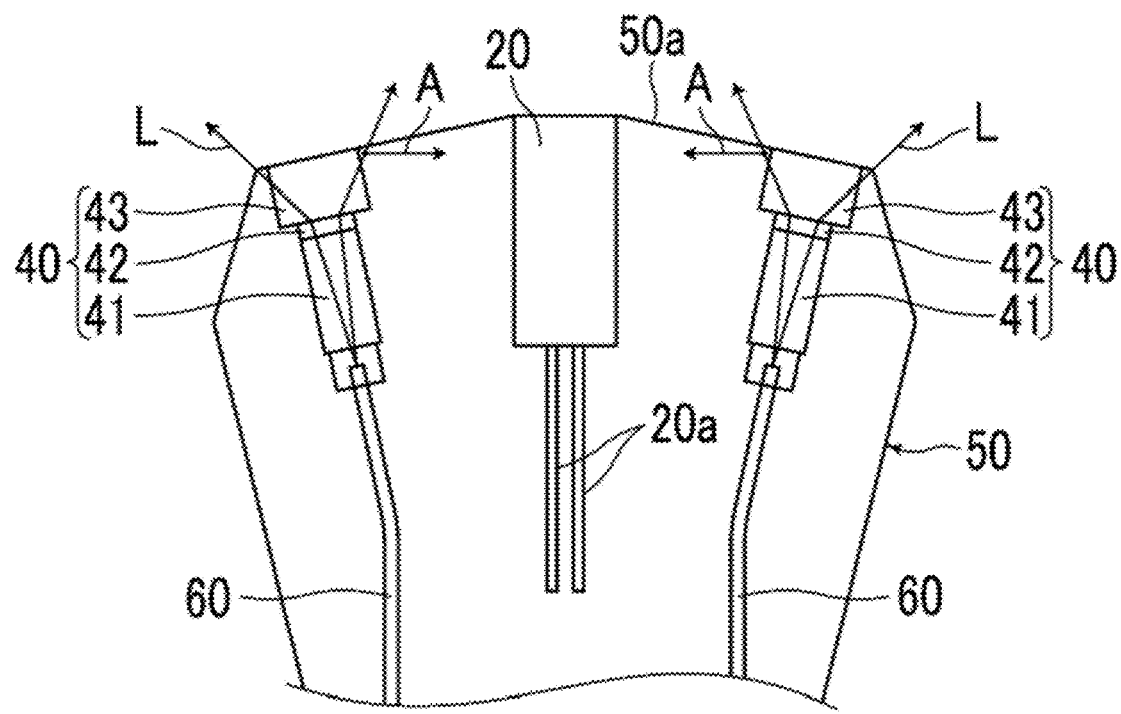
FIG. 12 is a side sectional view showing an example of a conventional probe.

FIG. 12 shows an example of a conventional probe not having the slit 45 described above. FIG. 12 shows a side sectional shape of the probe. In FIG. 12, the same elements as in FIG. 2 described previously are denoted by the same reference numerals, and the explanation thereof will be omitted unless particularly required (the same hereinbelow). According to the research by the inventors of the present invention, it was found that artifacts could be generated by the following reasons in the photoacoustic measurement apparatus using the conventional probe. That is, as shown in FIG. 12, when measurement light (laser light) L is emitted from the light emitting unit 40, the measurement light L may be emitted to the vicinity of the surface of the housing 50. Then, a photoacoustic wave may be generated from a portion of the housing 50 that has absorbed the measurement light L as schematically indicated by an arrow A in the diagram, and the photoacoustic wave may be detected by the transducer array 20 to cause artifacts.

The photoacoustic measurement probe of the present invention was obtained based on the above-mentioned new finding. Specifically, in the probe 11 of the present embodiment, photoacoustic waves generated as described above are attenuated by the slit 45 provided between the transducer array 20 and the light emitting unit 40. That is, on two side surfaces of one slit 45 (a side surface on the transducer array 20 side and a side surface on the light emitting unit 40 side), air inside the slit is in contact with the material of the housing 50. The acoustic impedances of the two side surfaces are greatly different from each other. Therefore, photoacoustic waves that are generated in the vicinity of one light emitting unit 40 and travel toward the transducer array 20 are reflected and attenuated on the two side surfaces of the slit 45. For this reason, high-intensity photoacoustic waves do not reach the transducer array 20. This also applies to photoacoustic waves that are generated in the vicinity of the other light emitting unit 40 and travel toward the transducer array 20.

More specifically, the acoustic impedance of air is about 440 Pa·s/m, and the acoustic impedance of the material of the housing 50 is $2.3 \times 10^6$ Pa·s/m in a case where the material of the housing 50 is, for example, acrylonitrile butadiene styrene copolymerized synthetic resin (ABS).

As described above, in the case of generating and displaying a photoacoustic image using the probe 11 of the present embodiment, generation of artifacts in the photoacoustic image is prevented.

Figure 13:
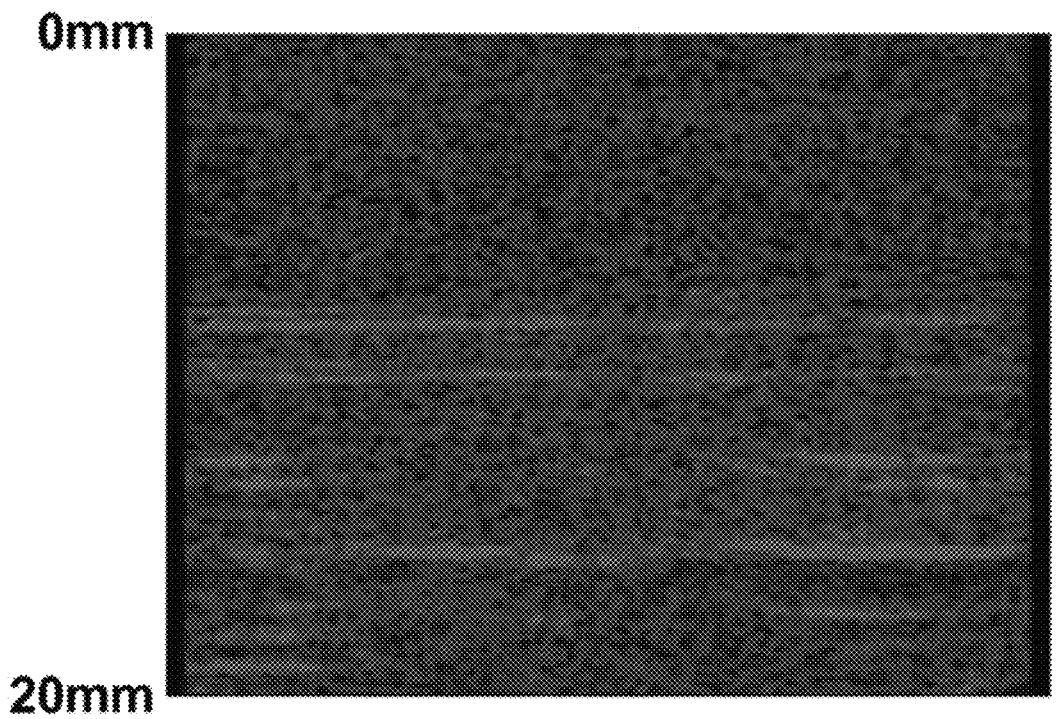
FIG. 13 is a diagram showing an example of a photoacoustic image obtained using a conventional probe.
Figure 14:
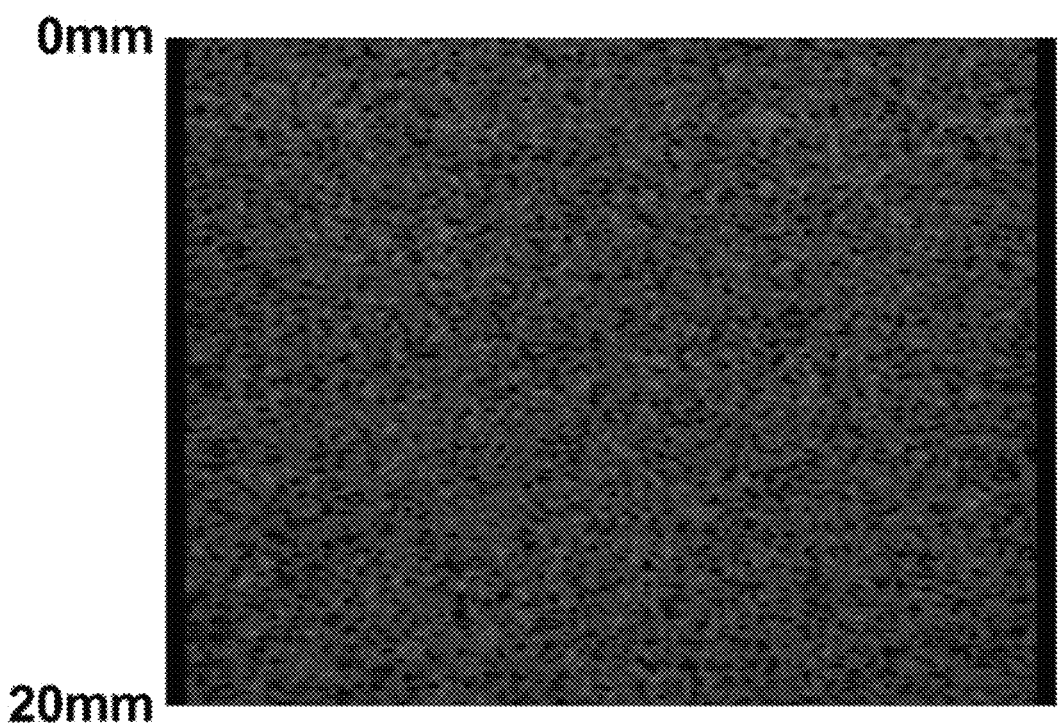
FIG. 14 is a diagram showing an example of a photoacoustic image obtained using a probe of the present invention.

FIGS. 13 and 14 show results of checking those described above by actually generating and displaying a photoacoustic image (tomographic image). FIG. 13 is a photograph showing a photoacoustic image generated using a conventional probe having the same configuration as the probe 11 of the present embodiment except that the slit 45 is not provided, and FIG. 14 is a photograph showing a photoacoustic image generated using the probe 11 of the present embodiment. Both the photoacoustic images are background images subjected to emphasis processing, and the numbers shown on the left side of each diagram indicate a distance from the probe surface, that is, the depth position of the subject. In the image shown in FIG. 13, horizontal striped artifacts are observed from a position near the depth of 10 mm to a position of 20 mm. In contrast, in the image shown in FIG. 14, such obvious artifacts are not observed.

In the probe 11 of the present embodiment, as clearly shown in FIG. 3, the length of each slit 45 is larger than the length of the transducer array 20. That is, in a plan view of the probe 11 from the surface (front surface), both end portions of the slit 45 are located outside both end portions of the transducer array 20 in a direction (left and right direction in FIG. 3) perpendicular to the arrangement direction of the light emitting unit 40 and the transducer array 20. By adopting such a configuration, photoacoustic waves generated near the side end portion of the light emitting unit 40 are reliably incident on the slit 45 to be attenuated.

Second Embodiment

Figure 4:
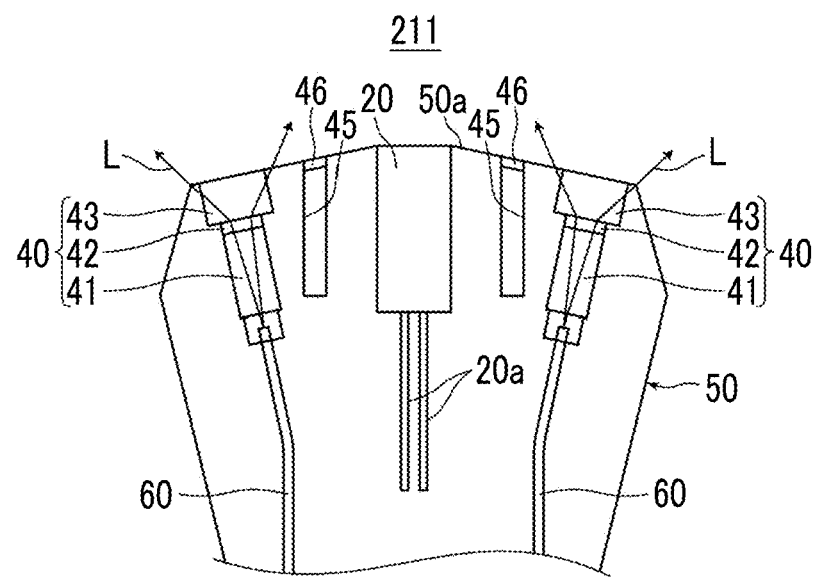
FIG. 4 is a side sectional view showing a probe according to a second embodiment of the present invention.

Next, a probe 211 according to a second embodiment of the present invention will be described with reference to FIG. 4. FIG. 4 shows the side sectional shape of the probe 211 of the present embodiment. Also in the probe 211, two slits 45 similar to those in the probe 11 described above are provided. A blocking member 46 is filled in a portion of each slit 45 close to the housing surface 50a. The surface of each blocking member 46 is even with the housing surface 50a, and the blocking member 46 is disposed in close contact with the housing 50. By disposing such a blocking member 46, it is possible to prevent foreign matters or the like from entering the slit 45.

The blocking member 46 is formed of a material having an acoustic impedance different from that of the material of the housing 50. As a combination of such two materials, the material of the housing 50 is ABS resin and the material of the blocking member 46 is silicone rubber. However, the materials are not limited thereto. In the above-described example, the acoustic impedance of the former material is about $2.3 \times 10^6$ Pa·s/m, and the acoustic impedance of the latter material is about $1.2 \times 10^6$ Pa·s/m to $1.5 \times 10^6$ Pa·s/m. The blocking member 46 is preferably a material having a high sound attenuation rate.

In the probe 211 of the present embodiment having the above configuration, photoacoustic waves are reflected and attenuated by a portion of the slit 45 where the blocking member 46 is not present, as in the probe 11 of the first embodiment.

In addition to this, also in the portion of the slit 45 where the blocking member 46 is present, the effect of attenuating the photoacoustic wave can be obtained. That is, at both end portions (an end portion on the transducer array 20 side and an end portion on the light emitting unit 40 side) of each blocking member 46, there is an interface where two materials having different acoustic impedances are in close contact with each other. These two interfaces extend toward the inside of the housing from the housing surface 50a. Therefore, when photoacoustic waves generated in the vicinity of one light emitting unit 40 propagate through the blocking member 46 to travel toward the transducer array 20, the photoacoustic waves are reflected and attenuated at the above two interfaces. For this reason, photoacoustic waves do not reach the transducer array 20 with high intensity. This also applies to photoacoustic waves that are generated in the vicinity of the other light emitting unit 40 and travel toward the transducer array 20.

As described above, also in the case of generating and displaying a photoacoustic image using the probe 211 of the present embodiment, generation of artifacts in the photoacoustic image is prevented. A foamed or porous plastic member may be present in a slit side inner portion as viewed from the blocking member 46 shown in FIG. 4, specifically, below the blocking member 46 shown in FIG. 4. Since such a plastic member contains many interfaces having different acoustic impedances therein, another effect that photoacoustic waves are reflected and scattered in the member is obtained.

Third Embodiment

Figure 5:
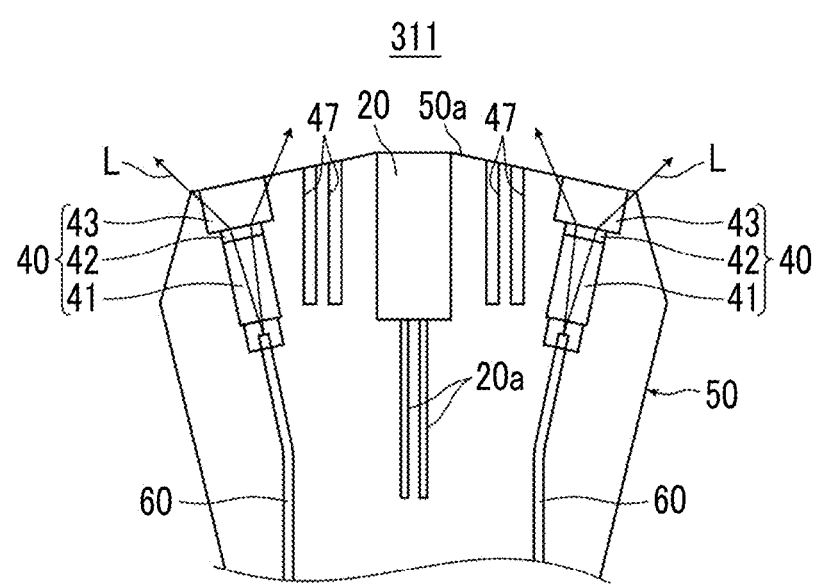
FIG. 5 is a side sectional view showing a probe according to a third embodiment of the present invention.

Next, a probe 311 according to a third embodiment of the present invention will be described with reference to FIG. 5. FIG. 5 shows the side sectional shape of the probe 311 of the present embodiment. In the probe 311, two slits 47 slightly smaller in width than the slit 45 in the probe 11 described above are provided between one light emitting unit 40 and the transducer array 20 and between the other light emitting unit 40 and the transducer array 20. Similarly to the slit 45 described above, the two slits 47 also reflect and attenuate photoacoustic waves that are generated in the vicinity of each light emitting unit 40 and travel toward the transducer array 20. Therefore, also in the case of generating and displaying a photoacoustic image using the probe 311 of the present embodiment, generation of artifacts in the photoacoustic image is prevented.

Fourth Embodiment

Figure 6:
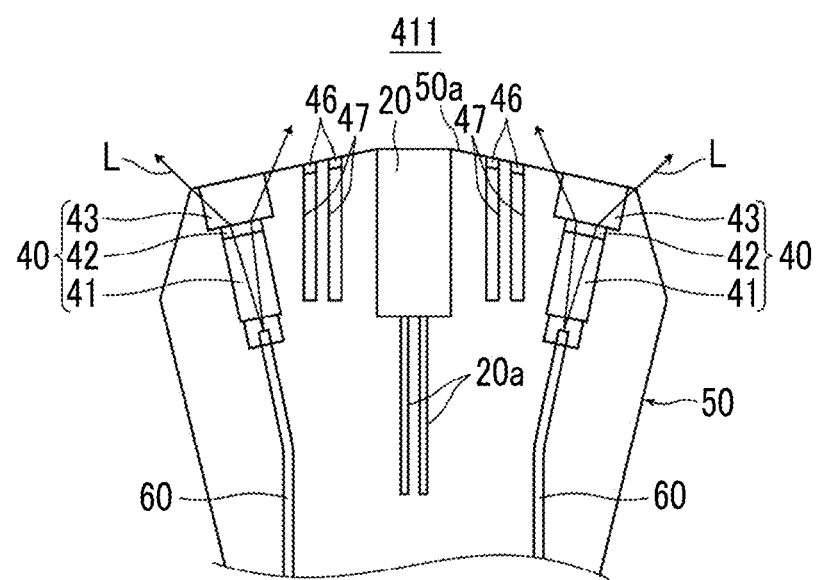
FIG. 6 is a side sectional view showing a probe according to a fourth embodiment of the present invention.

Next, a probe 411 according to a fourth embodiment of the present invention will be described with reference to FIG. 6. FIG. 6 shows the side sectional shape of the probe 411 of the present embodiment. In the probe 411, two slits 47 similar to those in the probe 311 of the third embodiment are provided between one light emitting unit 40 and the transducer array 20 and between the other light emitting unit 40 and the transducer array 20. The same blocking member 46 as in the second embodiment shown in FIG. 4 is filled in a portion of each of a total of four slits 47 close to the housing surface 50a. The surface of each blocking member 46 is even with the housing surface 50a, and the blocking member 46 is disposed in close contact with the housing 50.

By providing the slits 47 and disposing the blocking members 46 as described above, basically the same operation and effect as in the second embodiment can also be obtained in the present embodiment. In the present embodiment, in particular, four interfaces between two materials having different acoustic impedances are present between one light emitting unit 40 and the transducer array 20. Therefore, when photoacoustic waves generated in the vicinity of each light emitting unit 40 propagate through the blocking member 46 to travel toward the transducer array 20, the photoacoustic waves are reflected at the above interfaces a total of four times. As a result, the photoacoustic waves attenuate more largely. In addition, four interfaces between the material of the housing 50 and the air are also present between one light emitting unit 40 and the transducer array 20. Therefore, the reflection and attenuation of photoacoustic waves at these interfaces are also larger. As a result, also in the case of generating and displaying a photoacoustic image using the probe 411 of the present embodiment, generation of artifacts in the photoacoustic image is prevented.

Fifth Embodiment

Figure 7:
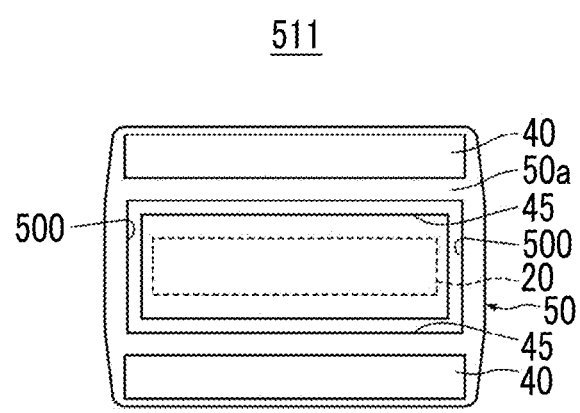
FIG. 7 is a front view showing a probe according to a fifth embodiment of the present invention.

Next, a probe 511 according to a fifth embodiment of the present invention will be described with reference to FIG. 7. FIG. 7 shows the front shape of the probe 511 of the present embodiment. In the probe 511, two slits 45 similar to those in the probe 11 of the first embodiment are provided between one light emitting unit 40 and the transducer array 20 and between the other light emitting unit 40 and the transducer array 20. One ends of the two slits 45 are connected to each other and the other ends of the two slits 45 are connected to each other by another slit 500. That is, the transducer array 20 is surrounded by the slit 45 and the slit 500 over the entire circumference.

In the configuration shown in FIG. 3, there is a possibility that the photoacoustic waves generated in the vicinities of both end portions (left and right end portions in FIG. 3) of each light emitting unit 40 will propagate outside both end portions of the slit 45 and then travel inward to reach the transducer array 20. In contrast, if the transducer array 20 is surrounded by the slits 45 and 500 as in the present embodiment, it is also prevented that the photoacoustic waves, which have traveled as described above, reaches the transducer array 20. In addition, the slit 500 may be discontinuous in the middle.

Therefore, in the case of generating and displaying a photoacoustic image using the probe 511 of the present embodiment, it is possible to reduce artifacts generated in the photoacoustic image more significantly compared with the case of generating and displaying a photoacoustic image using the probe 11 shown in FIG. 3.

Sixth Embodiment

Figure 8:
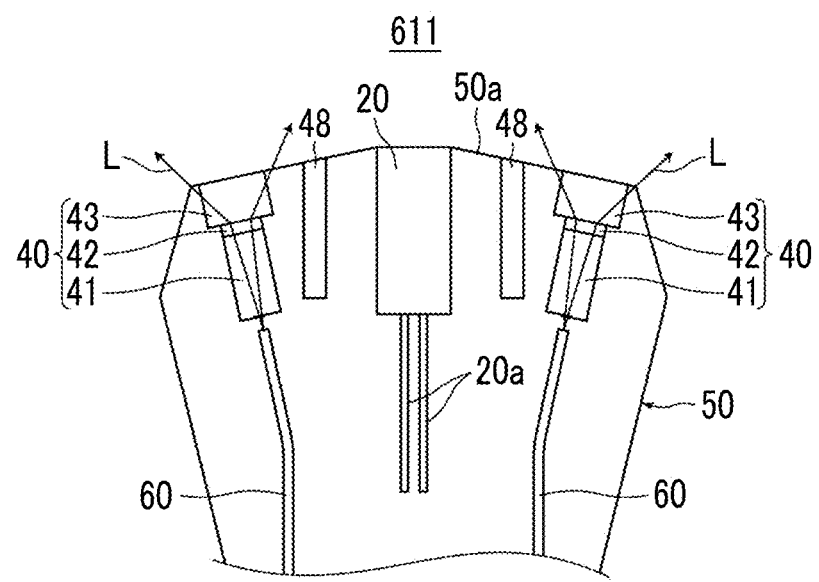
FIG. 8 is a side sectional view showing a probe according to a sixth embodiment of the present invention.

Next, a probe 611 according to a sixth embodiment of the present invention will be described with reference to FIG. 8. FIG. 8 shows the side sectional shape of the probe 611 of the present embodiment. In the probe 611, a blocking member 48 formed of a material having a different acoustic impedance from the material forming the housing 50 is provided between one light emitting unit 40 and the transducer array 20 and between the other light emitting unit 40 and the transducer array 20. As a combination of such two materials, the material of the housing 50 is ABS resin and the material of the blocking member 48 is silicone rubber. However, the materials are not limited thereto. In the above-described example, the acoustic impedance of the former material is about $2.3 \times 10^6$ Pa·s/m, and the acoustic impedance of the latter material is about $1.2 \times 10^6$ Pa·s/m to $1.5 \times 10^6$ Pa·s/m. The blocking member 48 is preferably a material having a high sound attenuation rate. As a material of the blocking member 48, a foamed or porous plastic member may be used. In addition, a combination of a plurality of members, such as silicone rubber in the upper portion of the blocking member 48 and a plastic member in the lower portion of the blocking member 48, may be used. Since such a plastic member contains many interfaces having different acoustic impedances therein, another effect that photoacoustic waves are reflected and scattered in the member is obtained.

The surface of the blocking member 48 is even with the housing surface 50a, and the blocking member 48 is disposed in close contact with the housing 50. Such a blocking member 48 can be formed, for example, by providing the same slit as the slit 45 shown in FIG. 2 in the housing 50 and then filling a material, which has an acoustic impedance different from that of the material forming the housing 50, in the entire slit. Alternatively, when the housing 50 is formed by, for example, injection molding, the blocking member 48 can be formed by embedding a material different from the housing material. In addition, the blocking member 48 can also be formed by modifying a part of the housing 50 after generating the housing 50.

On the outer side (light emitting unit 40 side) and the inner side (transducer array 20 side) of the blocking member 48, there is an interface where two materials having different acoustic impedances are in close contact with each other. These two interfaces extend toward the inside of the housing from the housing surface 50a. Therefore, as in the case where the blocking member 46 shown in FIG. 4 is provided, when photoacoustic waves generated in the vicinity of one light emitting unit 40 travel toward the transducer array 20, the photoacoustic waves are reflected and attenuated at the above two interfaces. For this reason, photoacoustic waves do not reach the transducer array 20 with high intensity. This also applies to photoacoustic waves that are generated in the vicinity of the other light emitting unit 40 and travel toward the transducer array 20.

As a result, also in the case of generating and displaying a photoacoustic image using the probe 611 of the present embodiment, generation of artifacts in the photoacoustic image is prevented.

Similarly to the slit 45 shown in FIG. 2, the blocking member 48 is formed such that both end portions of the blocking member 48 are located outside both end portions of the transducer array 20 in a direction perpendicular to the arrangement direction of the light emitting unit 40 and the transducer array 20. Accordingly, also at the interface between the blocking member 48 and the housing 50, both the end portions are located outside both the end portions of the transducer array 20. Therefore, photoacoustic waves generated in the vicinity of each of both the end portions of the light emitting unit 40 are reliably incident on the interface to be reflected and attenuated.

Similarly to the slits 45 and 500 shown in FIG. 7, the blocking member 48 may be formed so as to surround the periphery of the transducer array 20. In this case, since the interface between the blocking member 48 and the housing 50 also surrounds the periphery of the transducer array 20, it is prevented that photoacoustic waves travel inward from the end portion side of the transducer array 20 and are detected by the transducer array 20. The blocking member 48 (blocking member 48 disposed at a position corresponding to the slit 500) that is newly provided to surround the periphery of the transducer array 20 may be discontinuous in the middle.

Seventh Embodiment

Figure 9:
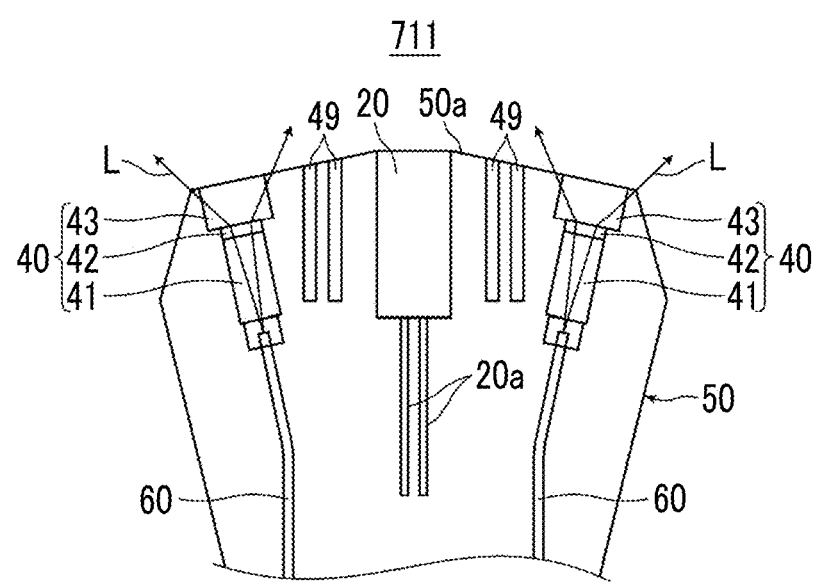
FIG. 9 is a side sectional view showing a probe according to a seventh embodiment of the present invention.

Next, a probe 711 according to a seventh embodiment of the present invention will be described with reference to FIG. 9. FIG. 9 shows the side sectional shape of the probe 711 of the present embodiment. The probe 711 is different from the probe 611 of the sixth embodiment shown in FIG. 8 in that two blocking members 49 thinner than the blocking member 48 are provided instead of one blocking member 48. These blocking members 49 are formed of a material having an acoustic impedance different from that of the material forming the housing 50.

Also in the probe 711 having the configuration described above, the same operation and effect as in the probe 611 of the sixth embodiment shown in FIG. 8 are obtained. In the present embodiment, in particular, four interfaces between two materials having different acoustic impedances are present between one light emitting unit 40 and the transducer array 20. Therefore, when photoacoustic waves generated in the vicinity of each light emitting unit 40 travel toward the transducer array 20, the photoacoustic waves are reflected at the above interfaces a total of four times. As a result, the photoacoustic waves attenuate more largely. As a result, also in the case of generating and displaying a photoacoustic image using the probe 711 of the present embodiment, generation of artifacts in the photoacoustic image is prevented.

Eighth Embodiment

Figure 10:
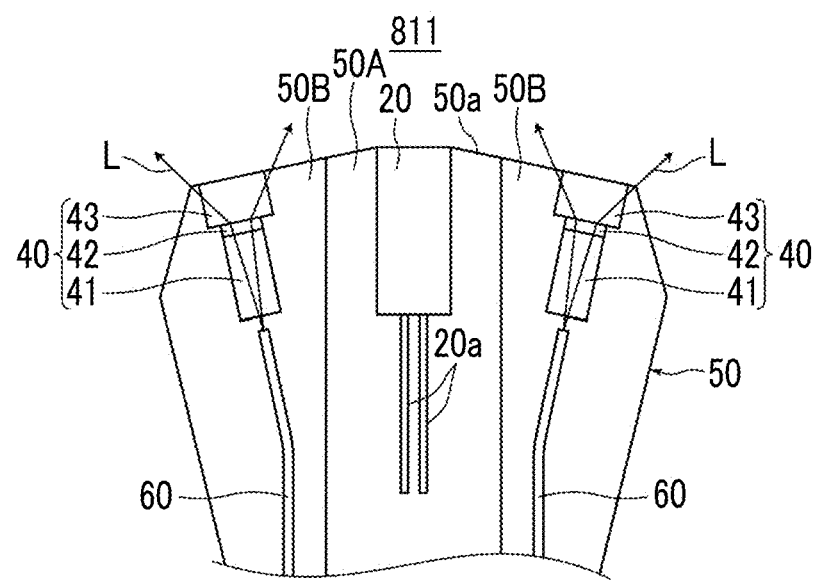
FIG. 10 is a side sectional view showing a probe according to an eighth embodiment of the present invention.

Next, a probe 811 according to an eighth embodiment of the present invention will be described with reference to FIG. 10. FIG. 10 shows the side sectional shape of the probe 811 of the present embodiment. The probe 811 is different from the probe 611 of the sixth embodiment shown in FIG. 8 in that the blocking member 48 is not provided and instead the housing 50 is configured to include two kinds of materials 50A and 50B. The housing materials 50A and 50B have different acoustic impedances. The housing material 50A is used for a portion that surrounds the transducer array 20, and the housing material 50B is used for a portion that is located outside the material 50A and surrounds the light emitting unit 40.

In the probe 811 having the configuration described above, one interface between the two housing materials 50A and 50B having different acoustic impedances is present between one light emitting unit 40 and the transducer array 20. Therefore, when photoacoustic waves generated in the vicinity of each light emitting unit 40 travel toward the transducer array 20, some of the photoacoustic waves are reflected and attenuated at the above interface. As a result, also in the case of generating and displaying a photoacoustic image using the probe 811 of the present embodiment, generation of artifacts in the photoacoustic image is prevented.

As a combination of the housing materials 50A and 50B, specifically, the housing material 50A is ABS resin and the housing material 50B is acrylic resin. However, the housing materials are not limited thereto. In the above-described example, the acoustic impedance of the housing material 50A is about $2.3 \times 10^6$ Pa·s/m, and the acoustic impedance of the housing material 50B is about $3.2 \times 10^6$ Pa·s/m.

As described above, also in the case of forming the housing 50 using the two housing materials 50A and 50B, a material having an acoustic impedance different from that of each housing material can be disposed in the housing material 50A or the housing material 50B, thereby further increasing the number of interfaces where two materials having different acoustic impedances are in close contact with each other. For example, if the blocking member 48 shown in FIG. 8 is disposed in the housing material 50B, three interfaces described above are present between the light emitting unit 40 and the transducer array 20.

Another member may be provided by providing a slit at the boundary between the housing materials 50A and 50B. In such a case, the slit may be configured so as to surround the transducer array 20. In a case where the above-described slit is not provided, the boundary between the housing materials 50A and 50B may be configured so as to surround the transducer array 20.

Ninth Embodiment

Figure 11:
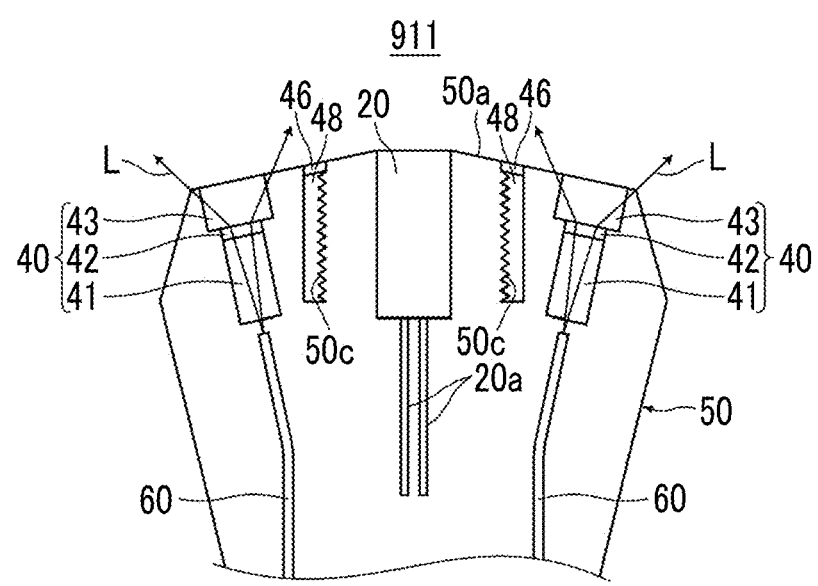
FIG. 11 is a side sectional view showing a probe according to a ninth embodiment of the present invention.

Next, a probe 911 according to a ninth embodiment of the present invention will be described with reference to FIG. 11. FIG. 11 shows the side sectional shape of the probe 911 of the present embodiment. The probe 911 is different from the probe 611 of the sixth embodiment shown in FIG. 8 in terms of the blocking member 46 being provided and the shape of a slit 50c of the housing 50. More specifically, the blocking member 46 is fixed to the housing 50 in a state in which the blocking member 46 is even with the housing surface 50a so as to cover the blocking member 48 from the probe surface side. The slit 50c receiving the blocking member 48 has a shape in which a plurality of pieces of roughness repeated in a slit depth direction so as to have a sawtooth cross section are provided on the inner side of the slit 50c, that is, on the wall surface on the transducer array 20 side.

In the present embodiment, as the blocking member 48, Novec (registered trademark) 7100 that is a fluorinated solvent of 3M Company or Fluorinert (registered trademark) FC-40 that is a fluorinated inert liquid of the company is appropriately used. Novec 7100 is one of hydrofluoroethers that are fluorinated liquids described above, and Fluorinert FC-40 is one of perfluorocarbons that are also fluorinated liquids. Even if the blocking member 48 is formed of a fluorinated liquid as described above, the blocking member 48 does not leak out of the housing 50 since the blocking member 46 is provided.

If the material of the housing 50 is ABS resin, the acoustic impedance is about $2.3 \times 10^6$ Pa·s/m as described above. In contrast, the acoustic impedance of Novec 7100 is $0.9 \times 10^6$ Pa·s/m, and the acoustic impedance of Fluorinert FC-40 is about $1.2 \times 10^6$ Pa·s/m. Accordingly, also in the present embodiment, on each of the outer side (light emitting unit 40 side) and the inner side (transducer array 20 side) of the blocking member 48, two interfaces where two materials having different acoustic impedances are in close contact with each other extend from the housing surface 50a toward the inside of the housing.

Therefore, also in the present embodiment, when photoacoustic waves generated in the vicinity of one light emitting unit 40 travel toward the transducer array 20, the photoacoustic waves are reflected and attenuated at the above two interfaces. For this reason, photoacoustic waves do not reach the transducer array 20 with high intensity. This also applies to photoacoustic waves that are generated in the vicinity of the other light emitting unit 40 and travel toward the transducer array 20. As a result, also in the case of generating and displaying a photoacoustic image using the probe 911 of the present embodiment, generation of artifacts in the photoacoustic image is prevented.

In the present embodiment, since a plurality of pieces of roughness described above are provided on the wall surface of the slit 50c, photoacoustic waves traveling toward the transducer array 20 are scattered by the pieces of roughness. Accordingly, even if the photoacoustic waves reach the transducer array 20, the photoacoustic waves are scattered. From this point, the generation of artifacts described above is more reliably prevented.

The subject M is generally a living body, such as a human body. Since a living body usually contains a lot of water, the sound speed in the living body at normal temperature is approximately the same as the sound speed of 1450 m/s to 1560 m/s in water. In contrast, the sound speed in Novec 7100 and the sound speed in Fluorinert FC-40 are 599.0 m/s and 636.4 m/s, respectively, which are about 40% of the sound speed in water. Therefore, for example, when it is necessary to generate and observe a photoacoustic image from the living body surface to a depth of 30 mm, it is preferable that the slit 50c filled with the blocking member 48 has a depth of about 12 mm (=30 mm×0.4) from the housing surface 50a. In a case where the probe 11 is of a handheld type, the above-described depth of the slit 50c does not particularly prolong the probe 11. Accordingly, the probe 11 has a reasonable size.

On the other hand, it is also conceivable to form the blocking member 48 using a general resin having an acoustic impedance different from that of the above-described ABS resin (for example, about 2.8×10⁶ Pa·s/m). The sound speed in the general resin is usually around 2000 m/s. Accordingly, in the case of forming the blocking member 48 using such a general resin, a resin material thickness of about 40 mm is required in order to generate a photoacoustic image from the living body surface to a depth of 30 mm in the same manner as described above. Hereinafter, the reason will be described.

Assuming that the propagation distance is X(m) and the sound speed in the propagation medium is V (m/s), the observation time T of the photoacoustic wave, that is, the time T(s) required until the photoacoustic wave is detected by the transducer array 20 after the photoacoustic wave is generated can be generally calculated by the following Equation (1).

$$T=X/V(s) \quad (1)$$

The observation time T of the photoacoustic wave generated at the depth position of 30 mm from the living body surface is calculated as $T=0.03/(1500 \text{ m/s})=2\times10^{-5}$ s using Equation (1) since the sound speed in the living body, which is mainly the human body, is around 1500 m/s. Here, it is considered that artifacts generated from the probe housing 50 are displayed at the depth position of 30 mm or more from the living body surface in the photoacoustic wave image. Assuming that the sound speed V in the housing 50 is 2000 m/s as described above, the propagation distance X of the housing 50 becomes $X=T \cdot V=(2\times10^{-5} \text{ s})\times(2000 \text{ m/s})=0.04$ m=40 mm using Equation (1) and the observation time T of the photoacoustic wave generated at the depth position of 30 mm from the living body surface.

Therefore, if the blocking member 48 is filled over the entire length of the slit 50c, the depth of the slit 50c is required to be about 40 mm. In a case where the probe 11 is of a handheld type, if the depth of the slit 50c is required to be about 40 mm, the probe 11 becomes remarkably long for that reason. Accordingly, the probe 11 is very difficult to use as a hand-held type probe.

In all of the probes of the embodiments described above, one light emitting unit 40 is disposed on each of both sides of the transducer array 20, which is an acoustic wave detection element, with the transducer array 20 interposed therebetween. However, the present invention is not limited to such probes, and the present invention can also be applied to a probe in which a plurality of light emitting units are disposed on at least one of both sides of one acoustic wave detection element, a probe in which only one acoustic wave detection element and one light emitting unit are provided, or a probe in which a plurality of acoustic wave detection elements are provided.

Figure 15:
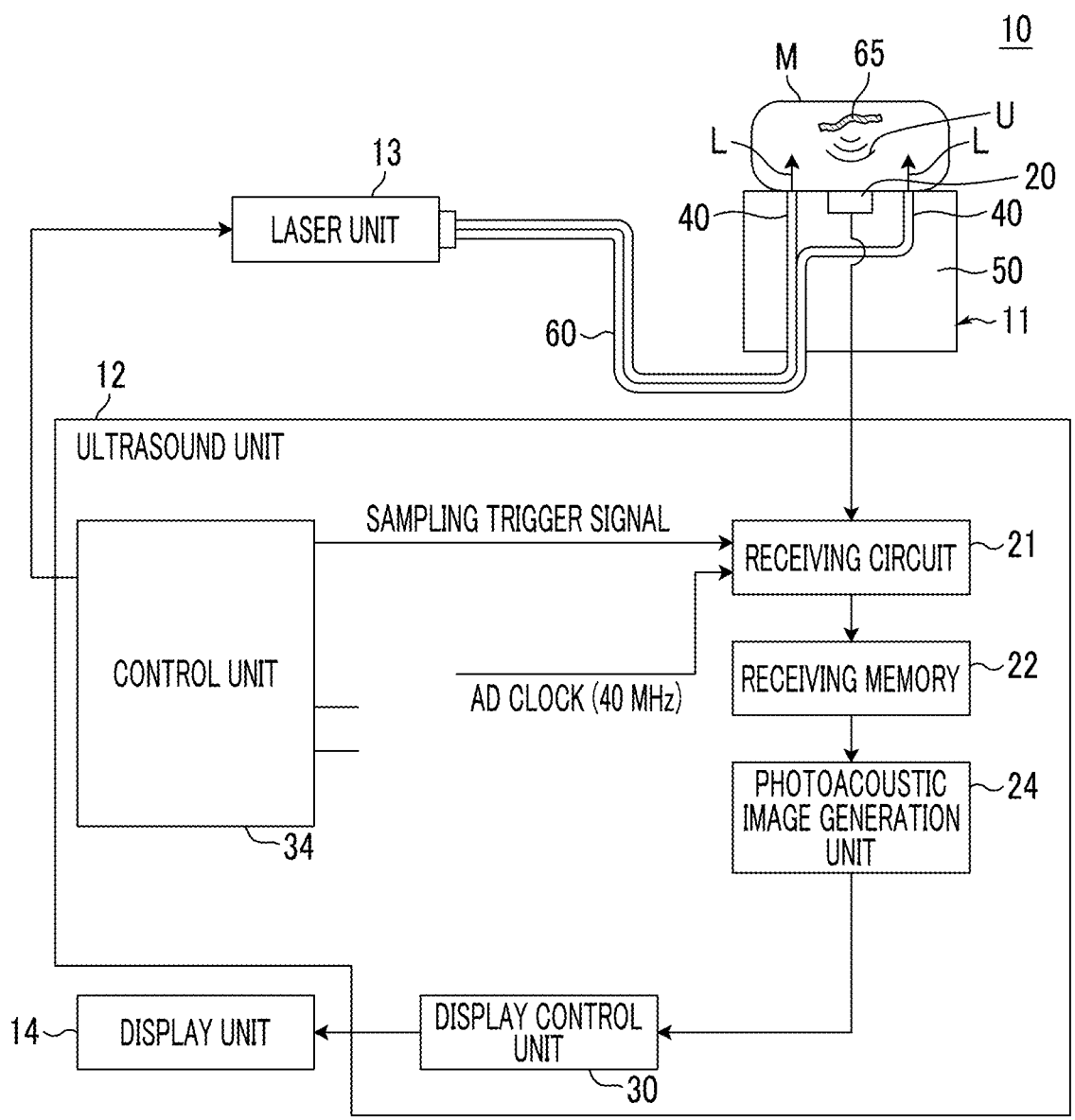
FIG. 15 is a schematic diagram showing the overall configuration of a photoacoustic measurement apparatus according to another embodiment of the present invention.

In addition, although the probe 11 applied to the photoacoustic measurement apparatus 10 capable of generating and displaying not only a photoacoustic image but also a reflected ultrasound image has been described, it is of course possible to apply the probe of the present invention to a photoacoustic measurement apparatus configured not to generate and display a reflected ultrasound image but only to generate and display a photoacoustic image. FIG. 15 shows an example of the photoacoustic measurement apparatus 10 configured as described above. The photoacoustic measurement apparatus 10 shown in FIG. 15 has a configuration in which the data separation means 23, the ultrasound image generation unit 29, and the transmission control circuit 33 are removed compared with that shown in FIG. 1.

In addition, the photoacoustic measurement apparatus 10 described above is configured to generate and display a photoacoustic image. However, the probe of the present invention is not limited to such a photoacoustic measurement apparatus, and can be applied to all photoacoustic measurement apparatuses that perform certain measurement based on the detected photoacoustic wave. That is, if the probe of the present invention is applied to the photoacoustic measurement apparatus, it is widely prevented that artifacts have an adverse effect on the measurement result as described above.

EXPLANATION OF REFERENCES

10: photoacoustic measurement apparatus
11, 211, 311, 411, 511, 611, 711, 811, 911: probe
12: ultrasound unit
13: laser unit
14: display unit
20: transducer array
21: receiving circuit
22: receiving memory
23: data separation means
24: photoacoustic image generation unit
29: ultrasound image generation unit
30: display control unit
33: transmission control circuit
34: control unit
40: light emitting unit
45, 47, 50c, 500: slit
46, 48, 49: blocking member
50: housing
50a: surface of housing
50A, 50B: housing material
60: optical fiber
65: absorber
L: laser light (measurement light)
M: subject
U: acoustic wave

What is claimed is:
1. A photoacoustic measurement probe, comprising:
a light emitting unit that emits measurement light toward a subject;
an acoustic wave detection element that detects an acoustic wave emitted from a portion of the subject that has received the measurement light; and
a housing which has a surface facing the subject at the time of use and in which the light emitting unit and the acoustic wave detection element are housed,
wherein at least one slit that is opened to the surface and that extends from the surface of the housing toward an inside of the housing is provided between the light emitting unit and the acoustic wave detection element,
wherein
the light emitting unit, the housing, the slit, the housing and the acoustic wave detection element are arranged in this order in an arrangement direction of the light emitting unit and the acoustic wave detection element,
a material of the housing is an ABS resin and a material formed into the slit of the housing is a porous plastic or a combination of silicone rubber and a plastic,
a ratio of an acoustic impedance of the material formed into the slit of the housing to that of the material of the housing is 0.52 to 0.65, and
the surfaces of the material formed into the slit of the housing and the housing are on the same plane.

2. The photoacoustic measurement probe according to claim 1,
wherein both end portions of the slit are located outside both end portions of the acoustic wave detection element in a direction perpendicular to the arrangement direction of the light emitting unit and the acoustic wave detection element.

3. The photoacoustic measurement probe according to claim 2,
wherein one light emitting unit is disposed on one of a side of the acoustic wave detection element, or two light emitting units are disposed on each of both sides of the acoustic wave detection element with the acoustic wave detection element interposed therebetween.

4. The photoacoustic measurement probe according to claim 3,
wherein, in the slit provided between one of the light emitting units disposed on both sides of the acoustic wave detection element and the acoustic wave detection element and the slit provided between the other one of the light emitting units disposed on both sides of the acoustic wave detection element and the acoustic wave detection element, one ends of the slits are connected to each other and the other ends of the slits are connected to each other by another slits, such that the acoustic wave detection element is surrounded by the slits.

5. A probe unit, comprising:
the photoacoustic measurement probe according to claim 4;
a light source that outputs measurement light; and
a connection unit that optically connects the measurement light to the light emitting unit of the photoacoustic measurement probe.

6. A photoacoustic measurement apparatus, comprising:
the photoacoustic measurement probe according to claim 4; and
a signal processing unit that generates a photoacoustic image based on a photoacoustic wave detection signal output from the photoacoustic measurement probe.

7. A probe unit, comprising:
the photoacoustic measurement probe according to claim 3,
a light source that outputs measurement light; and
a connection unit that optically connects the measurement light to the light emitting unit of the photoacoustic measurement probe.

8. A photoacoustic measurement apparatus, comprising:
the photoacoustic measurement probe according to claim 3; and
a signal processing unit that generates a photoacoustic image based on a photoacoustic wave detection signal output from the photoacoustic measurement probe.

9. A probe unit, comprising:
the photoacoustic measurement probe according to claim 2;
a light source that outputs measurement light; and
a connection unit that optically connects the measurement light to the light emitting unit of the photoacoustic measurement probe.

10. A photoacoustic measurement apparatus, comprising:
the photoacoustic measurement probe according to claim 2; and
a signal processing unit that generates a photoacoustic image based on a photoacoustic wave detection signal output from the photoacoustic measurement probe.

11. The photoacoustic measurement probe according to claim 1,
wherein one light emitting unit is disposed on one of a side of the acoustic wave detection element, or two light emitting units are disposed on each of both sides of the acoustic wave detection element with the acoustic wave detection element interposed therebetween.

12. The photoacoustic measurement probe according to claim 11,
wherein, in the slit provided between one of the light emitting units disposed on both sides of the acoustic wave detection element and the acoustic wave detection element and the slit provided between the other one of the light emitting units disposed on both sides of the acoustic wave detection element and the acoustic wave detection element, one ends of the slits are connected to each other and the other ends of the slits are connected to each other by another slit, such that the acoustic wave detection element is surrounded by the slits.

13. A probe unit, comprising:
the photoacoustic measurement probe according to claim 12;
a light source that outputs measurement light; and
a connection unit that optically connects the measurement light to the light emitting unit of the photoacoustic measurement probe.

14. A photoacoustic measurement apparatus, comprising:
the photoacoustic measurement probe according to claim 12; and
a signal processing unit that generates a photoacoustic image based on a photoacoustic wave detection signal output from the photoacoustic measurement probe.

15. A probe unit, comprising:
the photoacoustic measurement probe according to claim 11;
a light source that outputs measurement light; and
a connection unit that optically connects the measurement light to the light emitting unit of the photoacoustic measurement probe.

16. A photoacoustic measurement apparatus, comprising:
the photoacoustic measurement probe according to claim 11; and
a signal processing unit that generates a photoacoustic image based on a photoacoustic wave detection signal output from the photoacoustic measurement probe.

17. A probe unit, comprising:
the photoacoustic measurement probe according to claim 1;
a light source that outputs measurement light; and
a connection unit that optically connects the measurement light to the light emitting unit of the photoacoustic measurement probe.

18. A photoacoustic measurement apparatus, comprising:
the photoacoustic measurement probe according to claim 1; and
a signal processing unit that generates a photoacoustic image based on a photoacoustic wave detection signal output from the photoacoustic measurement probe.

19. The photoacoustic measurement probe according to claim 1,
wherein the material forming the housing seals the opening of the slit.

* * * * *